US010914877B2

(12) United States Patent
Blair et al.

(10) Patent No.: US 10,914,877 B2
(45) Date of Patent: Feb. 9, 2021

(54) NANOPARTICLE LIGHT FILTERING METHOD AND APPARATUS

(71) Applicant: University of Utah Research Foundation, Salt Lake City, UT (US)

(72) Inventors: Steven M. Blair, Salt Lake City, UT (US); Pradeep Kasinadhuni, Hillsboro, OR (US); Steve McDaniel, Provo, UT (US); Bradley Jay Katz, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 16/251,510

(22) Filed: Jan. 18, 2019

(65) Prior Publication Data

US 2019/0154894 A1    May 23, 2019

Related U.S. Application Data

(60) Division of application No. 14/542,564, filed on Nov. 15, 2014, now Pat. No. 10,281,627, which is a
(Continued)

(51) Int. Cl.
*G02B 5/20*    (2006.01)
*G02C 7/10*    (2006.01)
(Continued)

(52) U.S. Cl.
CPC ............ *G02B 5/206* (2013.01); *G02B 5/008* (2013.01); *G02C 7/104* (2013.01); *G02C 7/108* (2013.01);
(Continued)

(58) Field of Classification Search
CPC ........ G02B 5/206; G02B 5/008; G02C 7/104; G02C 7/108; G02C 2200/10; B82Y 20/00; B82Y 30/00; B82Y 5/00
(Continued)

(56) References Cited

U.S. PATENT DOCUMENTS 4,527,183 A    7/1985 Anthony et al.
5,218,386 A    6/1993 Levien
(Continued)

FOREIGN PATENT DOCUMENTS

DE    102005044031    3/2007
DE    102007007777    6/2008
(Continued)

OTHER PUBLICATIONS

U.S. Appl. No. 16/445,085, dated Nov. 18, 2019, Notice of Allowance.
(Continued)

*Primary Examiner* — Kristina M Deherrera
(74) *Attorney, Agent, or Firm* — Workman Nydegger

(57) ABSTRACT

Implementations of the present invention relate to apparatuses, systems, and methods for blocking, attenuating, or filtering neuroactive wavelengths of the visible light spectrum and reducing or preventing the symptoms affiliated with exposure to those wavelengths. Nanoparticles of a predetermined composition, size, and structure are dispersed in a host medium to create an optical notch filter, thereby attenuating only a narrow range of the visible spectrum.

17 Claims, 11 Drawing Sheets

Related U.S. Application Data continuation-in-part of application No. 14/542,478, filed on Nov. 14, 2014, now Pat. No. 10,234,608.

(60) Provisional application No. 61/904,861, filed on Nov. 15, 2013.

(51) Int. Cl.
| | |
|---|---|
| G02B 5/00 | (2006.01) |
| B82Y 5/00 | (2011.01) |
| B82Y 30/00 | (2011.01) |
| B82Y 20/00 | (2011.01) |

(52) U.S. Cl.
CPC ............ B82Y 5/00 (2013.01); B82Y 20/00 (2013.01); B82Y 30/00 (2013.01); G02C 2202/10 (2013.01)

(58) Field of Classification Search
USPC .......................................... 359/885–892
See application file for complete search history.

(56) References Cited

U.S. PATENT DOCUMENTS

| | | | |
|---|---|---|---|
| 5,402,190 | A | 3/1995 | Waldman |
| 5,737,045 | A | 4/1998 | Abileah |
| 5,946,114 | A | 8/1999 | Loiseaux et al. |
| 6,420,032 | B1 | 7/2002 | Iacovangelo |
| 6,610,081 | B2 | 8/2003 | Saathoff |
| 7,380,940 | B2 | 6/2008 | Anderson et al. |
| 7,438,411 | B2 | 10/2008 | Payne et al. |
| 7,556,376 | B2 | 7/2009 | Ishak et al. |
| 7,854,505 | B2 | 12/2010 | Cunningham |
| 7,988,318 | B1 | 8/2011 | Smith |
| 8,345,364 | B2 | 1/2013 | Liberman et al. |
| 9,606,277 | B2 | 3/2017 | Blair et al. |
| 9,759,848 | B2 | 9/2017 | Blair et al. |
| 9,764,157 | B2 | 9/2017 | Blair et al. |
| 2002/0044254 | A1 | 4/2002 | Saathoff |
| 2003/0161257 | A1 | 8/2003 | Yusu et al. |
| 2004/0085660 | A1 | 5/2004 | Hara et al. |
| 2005/0149993 | A1 | 7/2005 | Panda et al. |
| 2005/0164169 | A1 | 7/2005 | Malak |
| 2006/0092374 | A1 | 5/2006 | Ishak |
| 2006/0158732 | A1 | 7/2006 | Ramadan |
| 2006/0189113 | A1 | 8/2006 | Vanheusden et al. |
| 2007/0298242 | A1 | 12/2007 | Huo |
| 2008/0065177 | A1 | 3/2008 | Casper et al. |
| 2008/0221674 | A1 | 9/2008 | Blum et al. |
| 2009/0022995 | A1 | 1/2009 | Graham et al. |
| 2010/0149483 | A1 | 6/2010 | Chiavetta, III |
| 2010/0246009 | A1 | 9/2010 | Polley |
| 2010/0328763 | A1 | 12/2010 | Seo et al. |
| 2011/0060062 | A1 | 3/2011 | Wang et al. |
| 2011/0075263 | A1 | 3/2011 | Liberman |
| 2011/0223255 | A1 | 9/2011 | Thiesen et al. |
| 2013/0062637 | A1 | 3/2013 | Reed et al. |
| 2013/0100443 | A1 | 4/2013 | Li et al. |
| 2013/0130018 | A1 | 5/2013 | Poncelet et al. |
| 2013/0258456 | A1 | 10/2013 | Hashimura |
| 2014/0135570 | A1 | 5/2014 | Blair et al. |
| 2014/0160569 | A1 | 6/2014 | Blair et al. |
| 2014/0303504 | A1 | 10/2014 | Stankovic et al. |
| 2014/0320806 | A1 | 10/2014 | Cohen-Tannoudji et al. |
| 2014/0327967 | A1 | 11/2014 | Blair et al. |
| 2015/0138661 | A1 | 5/2015 | Blair et al. |
| 2015/0168616 | A1 | 6/2015 | Blair et al. |
| 2015/0234207 | A1 | 8/2015 | Koifman |
| 2016/0282532 | A1 | 9/2016 | Le et al. |
| 2017/0336545 | A1 | 11/2017 | Blair et al. |
| 2020/0192011 | A1 | 6/2020 | Blair et al. |

FOREIGN PATENT DOCUMENTS

| | | |
|---|---|---|
| DE | 102011050870 | 12/2012 |
| JP | 2006523593 | 10/2006 |
| JP | 2007021473 | 2/2007 |
| JP | 2007199421 | 8/2007 |
| JP | 2008203377 | 9/2008 |
| JP | 2009526132 | 7/2009 |
| JP | 2009536549 | 10/2009 |
| JP | 2015-509742 A | 4/2015 |
| WO | 2002020079 | 3/2002 |
| WO | 2004021071 | 3/2004 |
| WO | 2004077453 | 9/2004 |
| WO | 2006097794 | 9/2006 |
| WO | 2007011331 | 1/2007 |
| WO | 2007133197 | 11/2007 |
| WO | 2009100195 | 8/2009 |
| WO | 2010111499 | 9/2010 |
| WO | 2012154535 | 11/2012 |
| WO | 2012177296 | 12/2012 |
| WO | 2013039117 | 3/2013 |
| WO | 2013084176 | 6/2013 |
| WO | 2014011581 | 1/2014 |
| WO | 2015073933 | 5/2015 |
| WO | 2016014713 | 1/2016 |

OTHER PUBLICATIONS

U.S. Appl. No. 16/251,510, filed Jan. 18, 2019, Blair et al.
International Search Report for PCT/US2014/065848 dated Mar. 5, 2015.
Willets et al. "Localized Surface Plasmon Resonance Spectroscopy and Sensing," Annual Review in Physical Chemistry, vol. 58, 2007, pp. 267-297.
Sahoo et al. "Residual Polyvinyl Alcohol Associated with Poly (D,L-lactide-co-glycolilde) Nanoparticles Affects Their Physical Properties and Cellular Uptake," Journal of Controlled Release, vol. 82, 2002, pp. 105-114.
Bogoslovov et al. Effect of Silica Nanoparticles on the Local Segmental Dynamics in Poly(vinyl acetate), Macromolecules, 2008, vol. 41, pp. 1289-1296.
Khlebtsov et al. "The Effect of the Size, Shape, and Structure of Metal Nanoparticles on the Dependence of Their Optical Properties on the Refractive Index ofa Disperse Medium," Optics and Spectroscopy, vol. 98, No. 1, 2005, pp. 77-83.
Hannibal et al. "Roles of PACAP-Containing Retinal Ganglion Cells in Circadian Timing," International Review of Cytology, 2006, vol. 251, pp. 1-39.
Czeisler "Sleep and Circadian Rhythms in Humans," Cold Spring Harbor Symposia on Quantitative Biology, 2007, 72:579-97.
Czeisler, "The Effect of Light on the Human Circadian Pacemaker," CIBA Foundation Symposium. 1995: 183:254-90.
Duffy et al. "Entertainment of the Human Circadian System by Light." Journal of Biological Rhythms, 2005 20(4): 326-38.
International Search Report and Written Opinion for PCT/US2012/021500 dated May 8, 2012.
Noseda et al. "A Neural Mechanism for Exacerbation of Headache by Light" Nature Neruoscience, 2010 13:2 239-45.
Good et al. "The Use of Tinted Glasses in Childhood Migraine Headache," Headache: The Journal of Head and Face Pain, 1991 31:8 533-6.
Blackburn "FL-41 Tint Improves Blink Frequency, Light Sensitivity, and Functional Limitations in Patients with Benign Essential Blepharospasm," Ophthalmology 2009 116(5) 997-1001.
Mure et al "Melanopsin Bistability: A Fly's Eye Technology in the Human Retina," PLoS One. 2009 4(6):e5991.
Satchidananda Panda et al., "Illumination of the Melanopsin Signaling Pathway," Science, 307 (2005).
Berson et al., "Phototransduction by Retinal Ganglion Cells That Set the Circadian Clock," Science, 295 (2002).
Balzers et al., "Design of Optical Minus Filters," Journal of the Optical Society of America, vol. 61, No. 3, (1971).
Wang et al., "Theory and Applications of Guided-Mode Resonance Filters," Applied Optics, vol. 32, No. 14, (1993).

(56) References Cited

OTHER PUBLICATIONS

Larouche et al., "OpenFilters: Open-Source Software for the Design, Optimization, and Synthesis of Optical Filters," Applied Optics, vol. 47, No. 13, (2008).
European Search Report for EP15151981 dated May 19, 2015.
European Search Report for EP12802027 dated Nov. 30, 2015.
Hoggan et al., "Thin Film Optical Notch Filter Spectacle Coatings for the Treatment of Migraine and Photophobia," In Press. Journal of Clinical Neuroscience, 2016.
Kojima et al., "UV-Sensitive Photoreceptor Protein OPN5 in Humans and Mice," PLoS One 6(10):e26388. doi: 10.1371/journal.pone. 0026388.
European Search Report for application no. 14861298.9 dated Jun. 2, 2017.
U.S. Appl. No. 13/979,876, dated Nov. 18, 2016, Notice of Allowance.
U.S. Appl. No. 14/160,374, dated May 8, 2017, Notice of Allowance.
U.S. Appl. No. 14/338,182, dated May 10, 2017, Notice of Allowance.
U.S. Appl. No. 14/542,478, dated Aug. 25, 2017, Office Action.
U.S. Appl. No. 14/542,478, dated Dec. 15, 2017, Final Office Action.
U.S. Appl. No. 14/542,478, dated Jun. 22, 2018, Office Action.
U.S. Appl. No. 14/542,478, dated Nov. 21, 2018, Notice of Allowance.
U.S. Appl. No. 14/542,564, dated Aug. 25, 2017, Final Office Action.
U.S. Appl. No. 14/542,564, dated Jan. 10, 2018, Office Action.
U.S. Appl. No. 14/542,564, dated Dec. 26, 2018, Notice of Allowance.
U.S. Appl. No. 15/673,264, dated Sep. 20, 2018, Office Action.
U.S. Appl. No. 15/673,264, dated Jan. 10, 2019, Final Office Action.
U.S. Appl. No. 15/673,264, dated Mar. 11, 2019, Notice of Allowance.
U.S. Appl. No. 16/445,085, dated Sep. 27, 2019, Office Action.
U.S. Appl. No. 16/445,085, dated Nov. 1, 2019, Notice of Allowance.
U.S. Appl. No. 14/542,564, dated Nov. 2, 2016, Restriction Requirement.
International Search Report and Written Opinion for PCT/US2015/041610 dated Oct. 2, 2015.
Office Action received for U.S. Patent Application No. 14/160,374, dated Apr. 7, 2016.
Office Action received for U.S. Appl. No. 14/542,564, dated Nov. 2, 2016.
U.S. Appl. No. 13/979,876, dated Feb. 25, 2016, Office Action.
U.S. Appl. No. 14/160,374, dated Apr. 7, 2016, Office Action.
U.S. Appl. No. 14/160,374, dated Oct. 20, 2016, Office Action.
U.S. Appl. No. 14/338,182, dated Nov. 29, 2016, Office Action.
U.S. Appl. No. 14/542,478 dated Jun. 2, 2017, Final Office Action.
U.S. Appl. No. 14/542,478, dated Nov. 3, 2016, Office Action.
U.S. Appl. No. 14/542,564, dated Nov. 2, 2016, Office Action.
U.S. Appl. No. 14/542,564, dated Jul. 30, 2018, Final Office Action.
Blackburn, Marcus K et al. "FL-41 tint improves blink frequency, light sensitivity, and functional limitations in patients with benign essential blepharospasm." Ophthalmology vol. 116,5 (2009): 997-1001. doi:10.1016/j.ophtha.2008.12.031.
Czeisler CA, Gooley JJ. Sleep and circadian rhythms in humans. Cold Spring Harb Symp Quant Biol. 2007;72:579-597. doi:10.1101/sqb.2007.72.064.
Czeisler CA. The effect of light on the human circadian pacemaker. Ciba Found Symp. 1995;183:254-302. doi:10.1002/9780470514597. ch14.
Duffy JF, Wright KP Jr. Entrainment of the human circadian system by light. J Biol Rhythms. 2005;20(4):326-338. doi:10.1177/0748730405277983.
Final Office Action received for U.S. Appl. No. 14/542,478, dated Dec. 15, 2017.
Final Office Action received for U.S. Appl. No. 14/542,478, dated Jun. 2, 2017.
Final Office Action received for U.S. Appl. No. 14/542,564, dated Aug. 25, 2017.
Final Office Action received for U.S. Appl. No. 14/542,564, dated Jul. 30, 2018.
Final Office Action received for U.S. Appl. No. 15/673,264, dated Jan. 10, 2019.
Good, P., Taylor, R. And Mortimer, M. (1991), The Use of Tinted Glasses in Childhood Migraine. Headache: The Journal of Head and Face Pain, 31: 533-536. doi:10.1111/j.1526-4610.1991.hed3108533. x.
Hannibal J. Roles of PACAP-containing retinal ganglion cells in circadian timing. Int Rev Cytol. 2006;251:1-39. doi:10.1016/S0074-7696(06)51001-0.
International Search Report and Written Opinion for PCT/US2018/044835 dated Oct. 12, 2018.
Mure LS, Cornut PL, Rieux C, et al. Melanopsin bistability: a fly's eye technology in the human retina. PLoS One. 2009;4(6):e5991. Published Jun. 24, 2009. doi:10.1371/journal.pone.0005991.
Noseda, Rodrigo et al. "A neural mechanism for exacerbation of headache by light." Nature neuroscience vol. 13,2 (2010): 239-45. doi:10.1038/nn.2475.
Office Action received for U.S. Appl. No. 13/979,876, dated Feb. 25, 2016.
Office Action received for U.S. Appl. No. 14/160,374, dated Apr. 7, 2016.
Office Action received for U.S. Appl. No. 14/160,374, dated Oct. 20, 2016.
Office Action received for U.S. Appl. No. 14/338,182, dated Nov. 29, 2016.
Office Action received for U.S. Appl. No. 14/542,478, dated Aug. 25, 2017.
Office Action received for U.S. Appl. No. 14/542,478, dated Jun. 22, 2018.
Office Action received for U.S. Appl. No. 14/542,478, dated Nov. 3, 2016.
Office Action received for U.S. Appl. No. 14/542,564, dated Jan. 10, 2018.
Office Action received for U.S. Appl. No. 14/542,564, dated Jun. 5, 2017.
Office Action received for U.S. Appl. No. 15/673,264, dated Sep. 20, 2018.
Office Action received for U.S. Appl. No. 16/445,085, dated Sep. 27, 2019.
U.S. Appl. No. 14/542,564 dated Jun. 5, 2017, Office Action.

NANOPARTICLE LIGHT FILTERING METHOD AND APPARATUS

CROSS-REFERENCE TO RELATED APPLICATIONS

This application claims priority to and is a divisional of U.S. patent application Ser. No. 14/542,564 entitled "NANOPARTICLE LIGHT FILTERING METHOD AND APPARATUS", filed Nov. 15, 2014, which claims priority to and is a continuation-in-part of U.S. patent application Ser. No. 14/542,478 entitled "NANOPARTICLE LIGHT FILTERING METHOD AND APPARATUS", filed Nov. 14, 2014, which claims priority to and the benefit of U.S. Provisional Patent Application Ser. No. 61/904,861 entitled "NANOPARTICLE LIGHT FILTERING METHOD AND APPARATUS", filed Nov. 15, 2013. All of the aforementioned applications are incorporated herein by reference in their entirety.

BACKGROUND

Generally, this invention relates to optical filtration. More specifically, the present invention relates to the reduction of physiologic responses to certain wavelengths of light using notch filters containing nanoparticles.

Various electromagnetic wavelengths can have physical effect on the human body. In particular, certain wavelengths within the visible spectrum are suspected to have Sa negative neurological effects when received by certain photoreceptors in the human eye. Distinct from the rods and cones of the human eye, the melanopsin ganglion cells are also known as intrinsically photoreceptive Retinal Ganglion Cells (ipRGCs) and are intrinsically photoreceptive cells contained in the retina. The cells are connected to certain pain pathways, as well as connected to the suprachiasmatic nucleus. The pain pathways of the thalamus are suspected to affect migraine headaches. Meanwhile, the ipRGCs' interaction with the suprachiasmatic nucleus participates in entrainment of circadian rhythms.

The melanopsin ganglion cells' interaction with pain pathways of the brain have been linked to photophobia. In contrast to the common usage of "phobia," this is not an irrational fear of light, but rather a physical sensitivity to light. Photophobia has been linked to causing or exacerbating migraine headaches or other light sensitive neurological conditions such as blepharospasm and traumatic brain injury (TBI). The blockage or attenuation of the wavelengths of light that are related to photophobia may have a number of positive benefits. Reducing photophobia in sensitive individuals may lessen or prevent migraine headaches and other negative health effects.

Circadian rhythms are the internal cycles of the body, which approximately synchronize the 24 hour day-night cycles of the earth. Circadian rhythms are important for sleep, moods, and nutrition, as this internal cycle determines when one will feel the need to sleep or eat. They can be very beneficial in keeping the body "on schedule," but may also become problematic to individuals who do not want their body to align with the local daylight schedule. For example, individuals who travel frequently may be able to avoid the effects of jetlag by preventing changes to their circadian rhythms due to briefly traveling to a locale in a differing time zone. Alternatively, individuals working in professions with non-daylight hour based schedules may want to avoid the effects of the sunlight on their circadian rhythm. For example, a doctor on a night-shift rotation may want to entrain their body with a circadian rhythm irrespective of the light or darkness during the hours they may be awake and active.

To block or attenuate the wavelengths that are negatively neuroactive, the current method is to wear lenses that attenuate light across much of the visible spectrum. This method, however, has significant detriments as the lenses will impair vision in low-light settings and distort colors in nearly all situations. It would be preferable to attenuate the light arriving at the eye only within the narrow range or ranges that are suspected to be neuroactive.

Thus, there are a number of benefits from the selective attenuation or filtering of neuroactive wavelengths of light that can be realized.

BRIEF SUMMARY

Implementations of the present invention address one or more of the foregoing or other problems in the art with compositions, devices, systems, and methods for blocking, attenuating, or filtering neuroactive wavelengths of the visible light spectrum and reducing or preventing the symptoms affiliated with exposure to those wavelengths.

In a first non-limiting embodiment incorporating the presently claimed invention, an optical filter may comprise nanoparticles dispersed in a host medium. The host medium may then be disposed on a substrate. The substrate may be transparent to light in the visible spectrum such that the only attenuation of light is due to the dispersion of nanoparticles in the host medium coating the surface.

In a second non-limiting embodiment, a method of manufacturing an optical notch filter comprises determining a desired central wavelength of the filter, determining a desired full width half maximum of the filter, and manufacturing the filter by varying a size of a plurality of nanoparticles, a composition of the nanoparticles, and a composition of a host medium in which the plurality of nanoparticles are located. The filter may be manufactured by a variety of deposition techniques including spin coating and dip coating.

In a third non-limiting embodiment, a method for reducing the frequency and/or severity of photophobic responses includes receiving an amount of light across a visible spectrum Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. For better understanding, the like elements have been designated by like reference numbers throughout the various accompanying figures. While some of the drawings may be schematic representations, at least some of the drawings may be drawn to scale. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
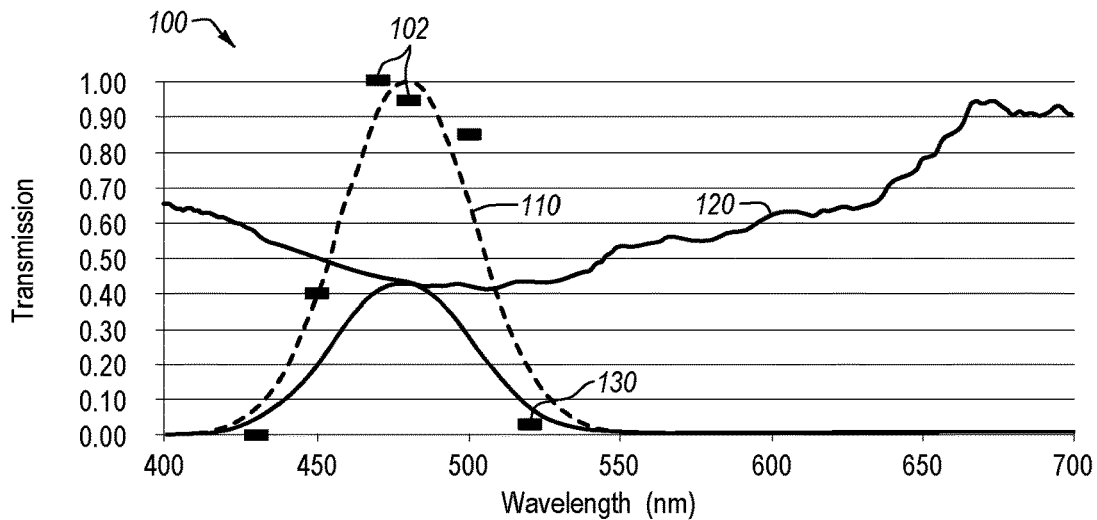
FIG. 1 is a graph depicting the melanopsin action potential response in relation to the transmission characteristics of a typical FL-41 35 filter prescribed to some patients with a photoresponsive medical condition.

One or more implementations of the present invention relate to the production of lenses, filters, other devices, or methods of blocking, attenuating, filtering or otherwise regulating the particular wavelengths of light that reach the human eye. In particular, the present invention is primarily concerned with the attenuation of neuroactive wavelengths that affect the melanopsin-containing ganglion cells in the retina of the eye. The melanopsin-containing ganglion cells are also known as the intrinsically photoreceptive Retinal Ganglion Cells, or ipRGCs and form the top layer of photoreceptive cells in the retina. When neuroactive wavelengths interact with the ipRGCs, transmissions are sent to a number of locations in the brain, aside from the image-processing centers. Included amongst those are the pain centers in the thalamus and the circadian rhythm control center in the suprachiasmatic nucleus, a collection of neurons in the brain's midline. The present invention is particularly concerned with the filtration or attenuation of the wavelengths that activate at least these nerve centers.

The neuroactive wavelengths can be regulated at the source or near the receptors in the eye. For example, a coating or filter may be placed across a screen or lens at the source to prevent the source from emitting the wavelengths. Alternatively or in addition, an individual may be able to filter the light approaching their eyes by, for example, wearing glasses that filter or attenuate particular wavelengths. There can be environmental considerations that dictate which method is preferable at the time. In a workplace, a large percentage of the neuroactive wavelengths may be produced simply by a computer monitor in front of an individual. An individual who is sensitive to particular wavelengths may be able to sufficiently reduce their exposure to that light by applying a filter to the computer screen directly. Similarly, a coating could be deposited on light bulbs or windows to attenuate the wavelengths at the source when indoors.

However, in another environment, simply reducing the emission of the neuroactive wavelengths at point sources may be insufficient to reduce an individual's exposure. For example, it may not be possible to reduce emissions from all sources in a building, or the primary source of the neuroactive wavelengths may be natural or ambient light, such as solar, rendering a source-based solution impossible. In such a situation, a sensitive individual may wear or otherwise use a filter adjacent or proximate their ipRGCs. The selective regulation of the wavelengths may be performed by a transparent surface. The filter may be integral to a lens, such as in sunglasses, or merely a coating on a lens, such as a thin coating applied to a conventional prescription lens used for vision correction. In such a manner, the individual may be able to wear eyeglasses or even contact lenses with neuroactive wavelength attenuating properties and effectively regulate nearly all light reaching the eye.

FIG. 1 depicts a graph 100 with an example of the estimated action potential spectrum for the ipRGCs. The solid points 102 on the graph 100 are the empirically measured response values for wavelengths, normalized to the maximum response, and the dashed line is a Gaussian distribution 110 fit to the response data. This Gaussian distribution 110 is not meant to be representative of the precise response spectrum of the ipRGCs, but rather an approximation of the depicted dataset. More refined data sets may become available regarding the response spectrum of ipRGCs, and it should be understood that the present disclosure is at least equally applicable to refined response spectra.

FIG. 1 also depicts the transmission characteristics 120 of the "FL-41 35" filter that is, currently, a commonly prescribed filter for regulating the transmission of light to photosensitive individuals in indoor environments. The FL-41 35 filter is created by impregnating a material with an organic dye to reduce the transmission of light through the material. As shown in FIG. 1, the filter transmits the lowest amount of incoming light at approximately 500 nm wavelengths, but transmits less than 70% of incoming light from 400 nm to 640 nm, corresponding to violet through orange colors in the visible light spectrum. Meanwhile, the photoreceptors in the ipRGCs are below a 5% response outside of 430 nm to 520 nm, as shown. Therefore, while the amount of light perceived 130 by the ipRGCs is significantly reduced by the FL-41 35 filter, the remainder of an individual's vision is also impaired.

Figure 2:
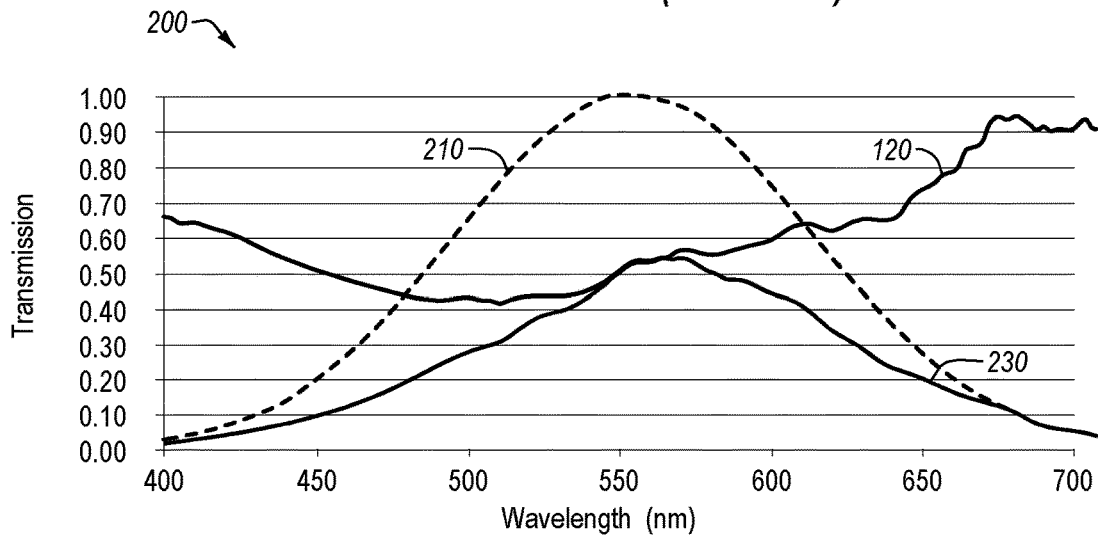
FIG. 2 is a graph depicting a typical human visual response spectrum in relation to the transmission characteristics of a typical FL-41 35 filter prescribed to some patients with a photoresponsive medical condition.

This effect is more fully visualized in FIG. 2. The graph 200 in FIG. 2 depicts the effect of the transmission characteristics 120 of the FL-41 35 filter on an individual's approximate overall visual response spectrum 210. The estimated effective visual response 230 is significantly impacted across the full width of the spectrum. In total, a FL-41 35 filter prevents transmission of about 47% of incoming light in a complete visible spectrum. Blocking the entirety of the visible light spectrum can lead to undesired effects such as distortions in perceived colorations and/or may diminish vision in low-light situations to an unacceptable level for a user. Furthermore, because the reduction in transmission is spread across the spectrum, the FL-41 35 filter is undesirable option when considering coatings for point sources.

Figure 3:
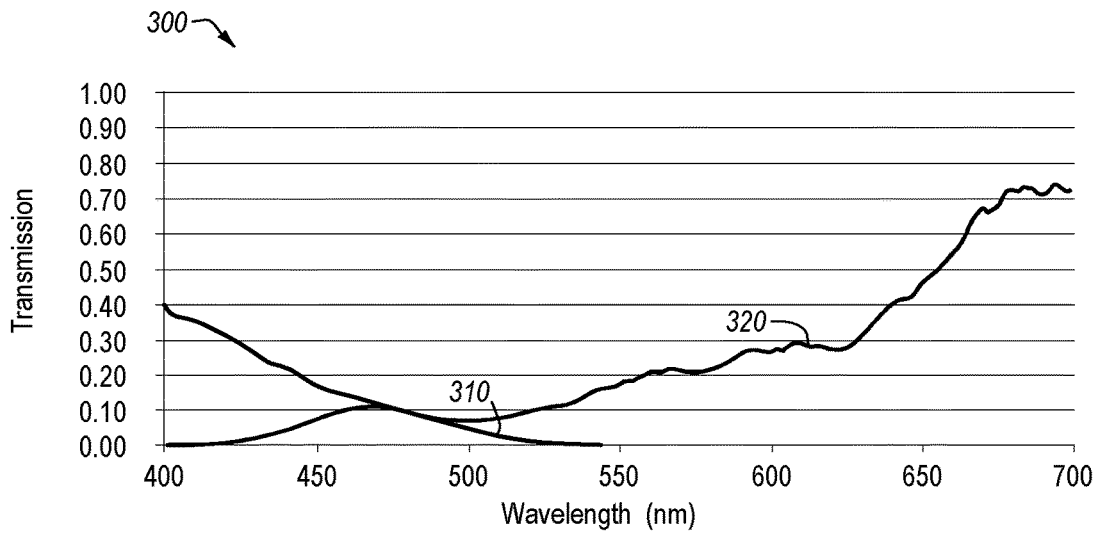
FIG. 3 is a graph depicting the melanopsin action potential response in relation to the transmission characteristics of a typical FL-41 55 filter prescribed to some patients with a photoresponsive medical condition.
Figure 4:
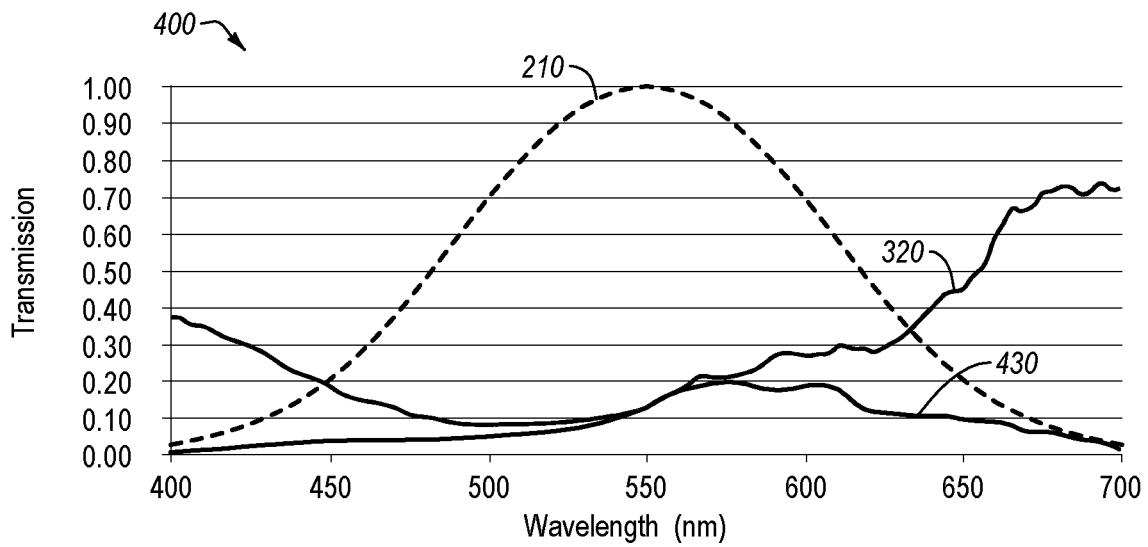
FIG. 4 is a graph depicting a typical human visual response spectrum in relation to the transmission characteristics of a typical FL-41 55 filter prescribed to some patients with a photoresponsive medical condition.

FIG. 3 depicts a graph 300 with an example of the estimated action potential spectrum 310 for the ipRGCs as inhibited by a FL-41 55 filter's transmission characteristic 320. The FL-41 55 is a version of the FL-41 35 filter with a higher amount of the transmission-blocking dye impregnated into the material. The FL-41 55 inhibits about 89% of light transmission in the range in which melanopsin cells are active, but the FL-41 55 filter also inhibits about 81% of the total spectrum from passing through the material, as can be seen in FIG. 4, which includes the visual response spectrum 210 overlaid. Because it transmits less light, the FL-41 55 filter is prescribed primarily for outdoor applications. However, this highlights one of several drawbacks to the FL-41 filter: the associated attenuation of other portions of the spectrum means that a user must change actual FL-41 filter from, for example a FL-41 35 filter to a FL-41 55 filter when transitioning from indoor environments to outdoors. Other drawbacks include the aforementioned color distortion and safety concerns in low-light situations, the requirement that the dye be mixed with only certain types of plastics, and difficulties with uniformity of the tinting process.

It is therefore desirable to produce a filter that will attenuate the neuroactive wavelengths while minimizing spectral distortion. Additional or other constraints on filter design may be considered, including optimization methods.

One method to evaluate the performance of optical filters in the context of blocking light absorption by melanopsin cells is presented here. The light dose D experienced by melanopsin cells can be written $$D_{melan} = \int L(\lambda) T(\lambda) M(\lambda) d\lambda$$

where L is the light spectrum (in terms of intensity, power, photons/sec, etc), T is the spectral transmission of a filter lying between the light source and the eye, and M is the normalized action potential response spectrum of melanopsin, as currently estimated from FIG. 1 as a Gaussian function centered at 480 nm with a full-width at half-maximum of 52 nm. For generality, it is assumed that L=1 so as not to limit discussion to any specific light source, however analyses may be performed for any light source of known spectrum. A similar dose can be calculated associated with the visual response spectrum $$D_{vis} = \int L(\lambda) T(\lambda) V(\lambda) d\lambda$$

where V represents the normalized visual response spectrum. The effect of an optical filter, such as the FL-41 tint, is to reduce the dose, as described by taking the ratio of dose calculated with the filter to dose without the filter. A figure of merit (FOM) can also be defined which compares the blocking of the melanopsin response to the blocking of the visual response spectrum $$FOM = \frac{1 - \frac{D_{melan}}{D_{melan}(T=1)}}{1 - \frac{D_{vis}}{D_{vis}(T=1)}}$$

where a value FOM>1 may be desirable. For example, the FL-41 tint may produce a value FOM≈1.

As shown in the above FOM equation, the value FOM will increase as the spectrum of the notch filter more closely approximates the visual response spectrum of the melanopsin and the ipRGCs. The numerator will approach 1 as the light dose $D_{melan}$ experienced by melanopsin cells with a filter approaches 0 when compared against the unfiltered light dose $D_{melan}(T=1)$. In contrast, the denominator will approach zero as the filter attenuates a smaller portion of the visible spectrum, thus causing the value FOM to become greater than 1. A value FOM>1 reflects a preferential filtering wavelengths within the melanopsin visual response spectrum over the rest of the visible spectrum.

A notch or band-stop filter is one that passes most wavelengths or frequencies unaltered, but will attenuate those within a narrow range to very low levels. A notch filter can be thought of as the opposite of a band-pass filter. A notch filter may have a high Q factor, corresponding to a narrow stopband. Optical filter technologies may include, among other technologies, dielectric multi-layers and nanoparticle coatings. The latter may include metallic nanoparticles, dielectric nanoparticles, semiconductor nanoparticles or quantum dots, magnetic nanoparticles, core-shell particles consisting of one material in the core and another serving as a shell. The nanoparticles may have a variety of shapes. Host materials may include polymers, sol-gels, glasses or similar transparent or translucent materials.

Figure 4A:
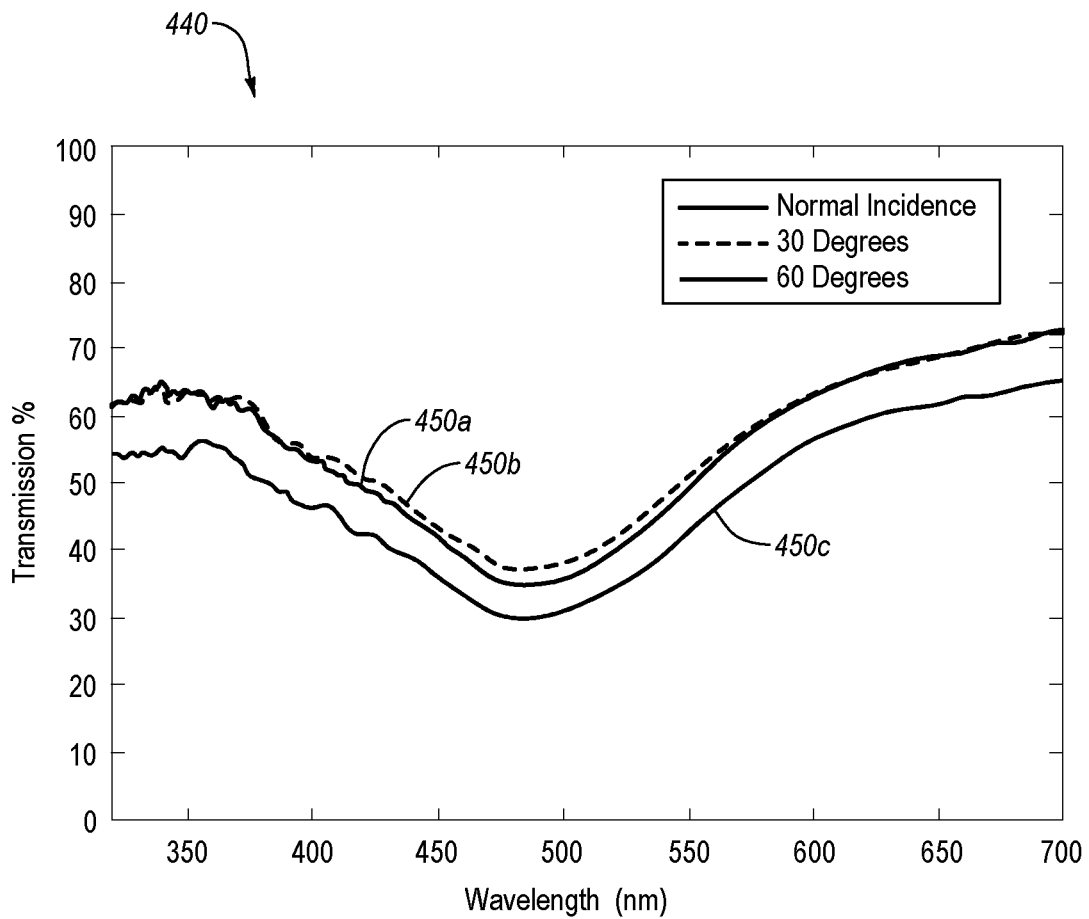
FIG. 4A is a graph depicting incident angle transmission.

The use of nanoparticles for wavelength attenuation has properties distinct from thin-film methods because the nanoparticles will scatter and absorb light irrespective of the incident angle of the light, as shown in graph 440 in FIG. 4A. The variation between the measured transmission of incident light that is normal 450a, 30° 450b, and 60° 450c to a surface of the filter, may be at least partially due to double interface reflection of 8%, 12%, and 31%, respectively for the optical filter. The double interface reflection coefficient may be calculated accruing to Fresnel equations. The calculated double interface reflection coefficients are in agreement with the measured transmission spectra. Because a nanoparticle notch filter will perform predictably regardless of the direction of light source, it is well suited for general purpose filtering, such as with eyeglass lenses. Furthermore, to accomplish the proper scattering and absorption of light, a number of parameters may be varied to optimize the range of wavelengths attenuated and the amount of attenuation and to tune the notch filter to different wavelengths.

A metallic nanoparticle may be excited by an incident light or other electromagnetic ("EM") radiation. The excitation of the metallic nanoparticle may result in the metallic nanoparticles exhibiting a collective oscillation of conduction electrons. A charge density oscillation of the conduction electrons is a localized surface plasmon ("LSP"). The LSP may enhance local electromagnetic fields during resonance of a plurality of LSPs excited by an incident selective wavelength of light. The resonant behavior of a plurality of LSPs is known localized surface plasmon resonance ("LSPR"). LSPR may provide large optical field enhancement and may lead to strong scattering and/or absorption of the incident wavelength. In simplified form, the frequency at which LSPR occurs may be given by:

$$\omega_{LSPR} = \frac{\omega_p}{(1 + 2\varepsilon_d)^{1/2}}$$

where $\omega_{LSPR}$ is the frequency at localized surface plasmon resonance, $\omega_p$ is the plasmon frequency of the metal and $\varepsilon_d$ is the dielectric constant of the environment surrounding the metallic nanoparticles. The LSPR wavelength and the peak width of the nanoparticle optical response may be sensitive to at least nanoparticle composition, size, shape, dielectric environment, proximity to other nanoparticles, or combinations thereof.

There may be scattering and absorption of incident light due to the high local field enhancement at the surface of nanoparticle at LSPR. The scattering of the light may be explained as the redirection of light that takes place when an electromagnetic (EM) wave encounters an obstacle (i.e., a nanoparticle). The absorption of the light can be explained by the amount of the incident light energy absorbed by the nanoparticle in the form of heat. The attenuation or loss of incident light through the combination of scattering and absorption of light is extinction. Nanoparticle dispersion on or within a transparent medium may allow for increased extinction at a variety of angles and amounts of incident light.

The extinction spectrum of a dispersion of nanoparticles may be modeled by a combination of approximations. Quasi static approximation may allow for modeling of the scattering and absorption coefficients of spherical dimension of size less than 1% of the wavelength of the incident light. Mie scattering theory (or Mie Theory) may provide approximations of the scattering and absorption coefficients of nanoparticles of other shapes and/or sizes. Mie Theory may provide a general framework enabling the exact solution to the scattering and absorption of light of a spherical particle.

Figure 5A:
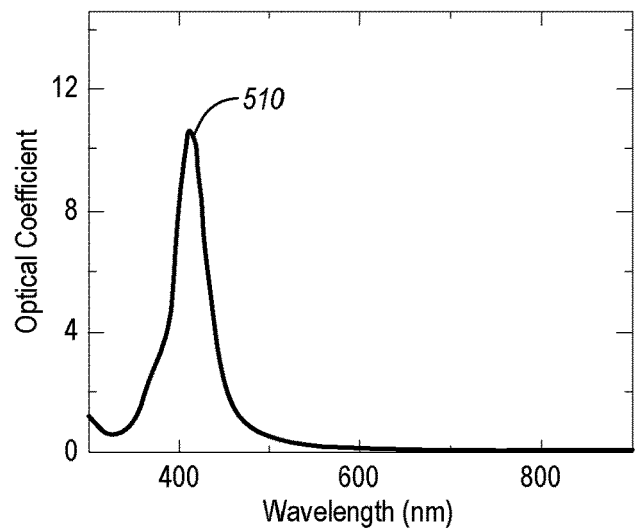
FIG. 5A is a simulated extinction spectrum for a 40 nm spherical nanoparticle.
Figure 5B:
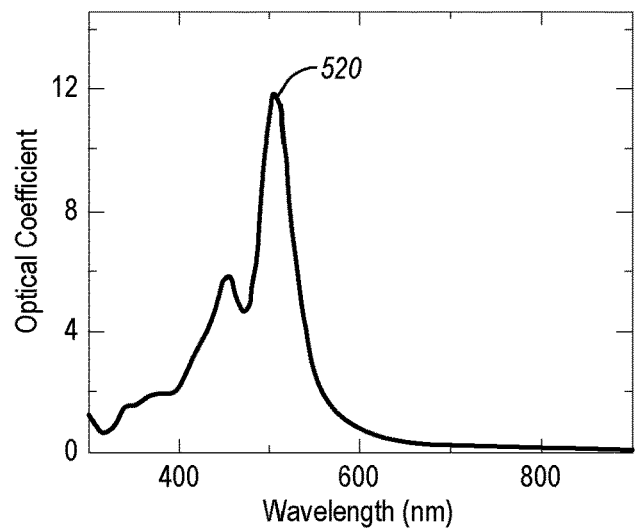
FIG. 5B is a simulated extinction spectrum for a 40 nm cubic nanoparticle.
Figure 5C:
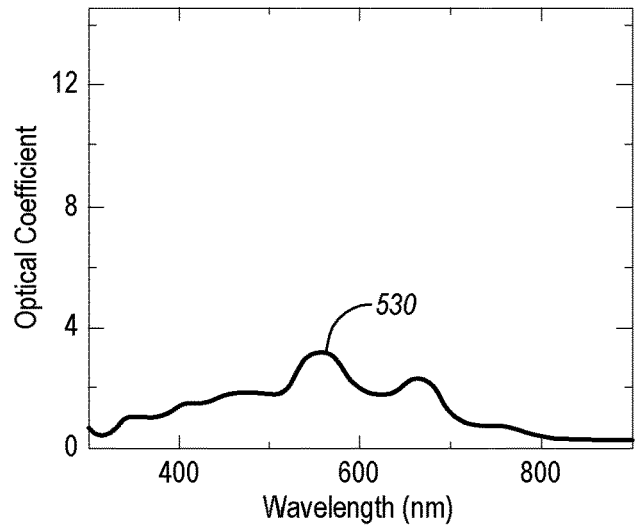
FIG. 5C is a simulated extinction spectrum for a 40 nm tetrahedral nanoparticle.
Figure 5D:
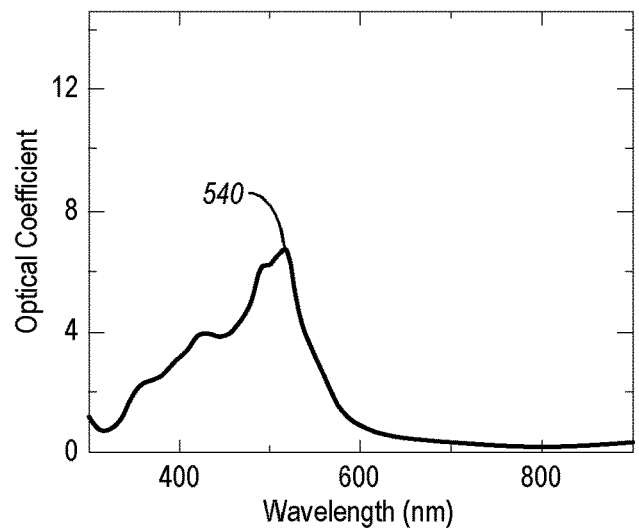
FIG. 5D is a simulated extinction spectrum for a 40 nm octagonal nanoparticle.
Figure 5E:
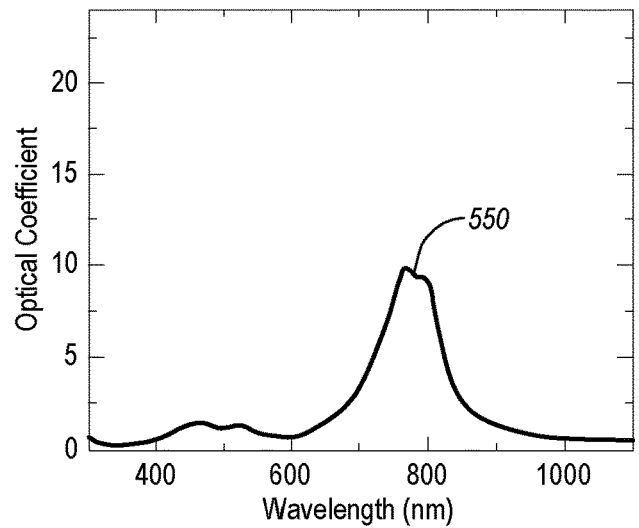
FIG. 5E is a simulated extinction spectrum for a 50 nm triangular nanoparticle that has a 5 nm thickness.
Figure 5F:
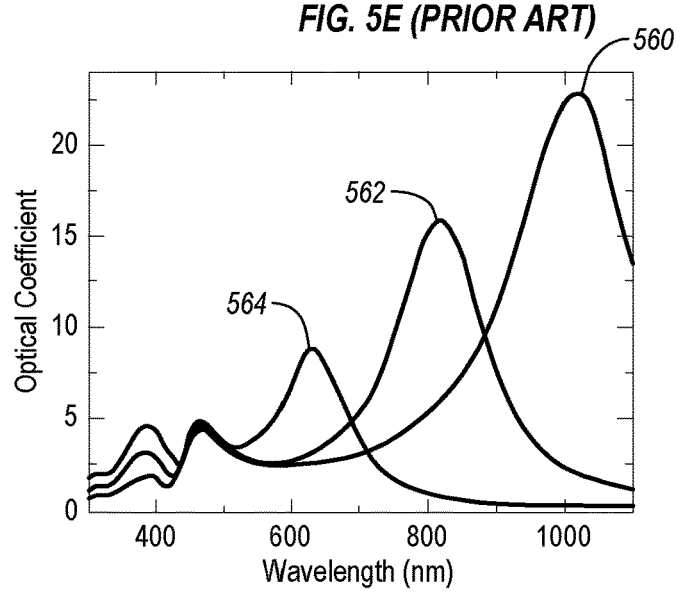
FIG. 5F is a series of simulated extinction spectra for 50 nm wide rectangular prism nanoparticles of different axial lengths.

As shown in FIGS. 5A-5F, the shape of a nanoparticle can have an effect on its extinction spectrum. A spherical particle spectrum 510, calculated based on spherical silver (Ag) nanoparticles having a 40 nm diameter, may have the most focused spectrum of the presented embodiments because they have a single, narrow primary peak that allows for optimization using size and composition changes, as shown in FIG. 5A. However, it may be possible to utilize a combination of particles of other shapes in order to develop a desired filter spectrum. In some embodiments, one may broaden the extinction spectrum of a 40 nm spherical nanoparticle filter by simply introducing, for example, 40 nm cubic nanoparticles or 40 nm octahedral nanoparticles. For example, FIG. 5B depicts a cubic particle spectrum 520 calculated based on cubic Ag nanoparticles having a 40 nm width. FIG. 5C depicts a tetrahedral particle spectrum 530 calculated based on tetrahedral Ag nanoparticles having a 40 nm width. FIG. 5D depicts an octahedral particle spectrum 540 calculated based on octahedral Ag nanoparticles having a 40 nm width along each edge. In other embodiments, one may introduce a second peak at a longer wavelength by introducing, for example, triangular plate nanoparticles. FIG. 5E depicts a triangular particle spectrum 550 calculated based on triangular plate Ag nanoparticles having a 40 nm width along the long edges and a thickness of 5 nm. The usage of varying particle shapes may be beneficial in tuning a spectrum of the nanoparticle filter. FIG. 5F depicts the extinction spectra of a 50 nm wide Ag prism with varying axial lengths. The longest axial length has the longest wavelength extinction spectrum 560, the medium axial length has the medium wavelength extinction spectrum 562, and the shortest axial length has the shortest wavelength extinction spectrum 564.

Figure 5G:
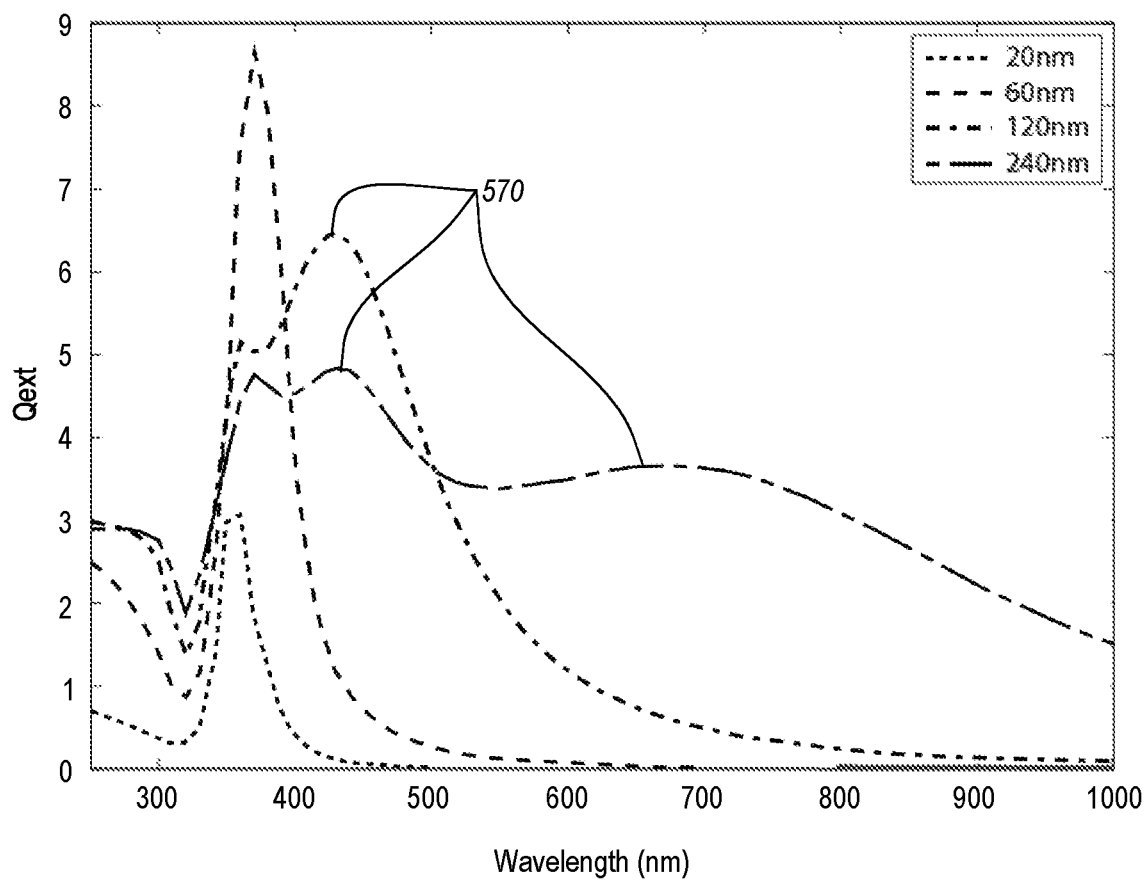
FIG. 5G is a graph depicting simulated extinction efficiencies for spherical particles of different diameters.

FIG. 5G depicts the simulated extinction spectrum for a spherical particle using Mie scattering theory for 20 nm, 60 nm, 120 nm, and 240 nm Ag particles. As one increases the diameter of a spherical nanoparticle, the spectral response may red-shift (moves towards a longer wavelength), the peak may broaden, and a higher order resonance mode at a shorter wavelength may become more pronounced. When the dimensions of the particle become comparable with to the wavelength of the light, the spectral position of the LSPR may red-shift with respect to that predicted by the electrostatic theory. A particle with dimensions closer to that of the incident wavelength of light may experience a retarded field, because the incident EM field is not continuous across the spherical particle, further leading to inhomogeneous polarization of the nanoparticle. The inhomogeneous polarization of the nanoparticle may lead to the excitation of the higher order resonant modes 570 visible in FIG. 5G. Therefore, it is beneficial to use particles less than about 100 nm in diameter, and even more preferable to use nanoparticles less than about 80 nm in diameter.

An ambient host material may also affect the extinction spectrum of the nanoparticle dispersion and an associated optical filter. For example, the scattering coefficients may be proportional to the relative index of the refraction of the host material. The position of the extinction spectrum may be at least partially dependent on the dielectric constant of the host material. As the refractive index of the host material in which the nanoparticles are embedded is increased, the spectral position of the LSPR red shifts, which may result in a narrower and greater extinction coefficient.

In an embodiment, a filter according to the present invention may use nanoparticles that absorb or reflect light in a narrow range to effectively block only that range of wavelengths. In an embodiment, the nanoparticles may be distributed in a bulk transparent host material. In another embodiment, the nanoparticles may be distributed within a transparent host material applied as a coating on a substrate. The substrate may be transparent, as well. For example, as shown in FIG. 6, the nanoparticles 620 may be distributed in a host material 610, or as shown in FIG. 7, the nanoparticles 720 may be suspended in a coating 710 deposited onto the surface of a substrate 750.

Figure 6:
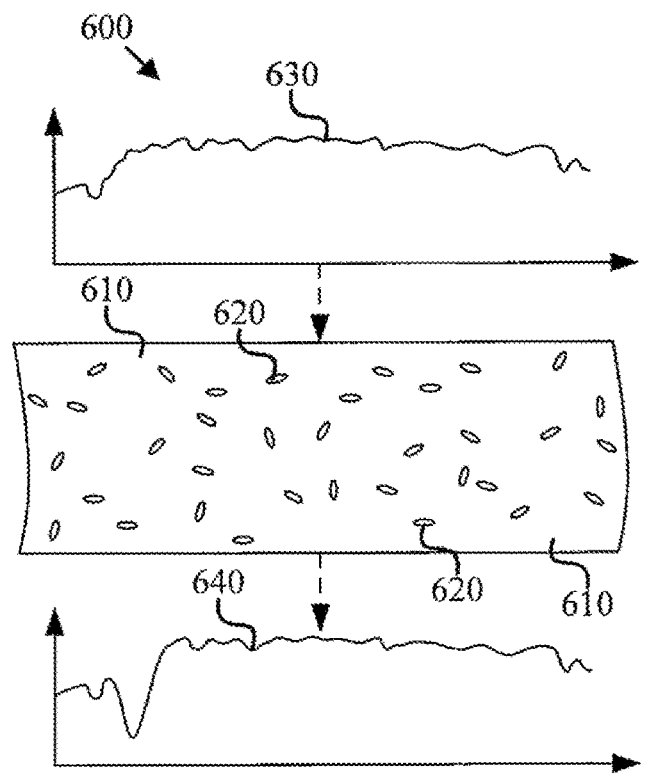
FIG. 6 is a schematic cross-sectional view illustration depicting one embodiment of a light filtering apparatus according to the present invention.

In FIG. 6, the nanoparticles 620 are depicted suspended in a host material 610 that is otherwise transparent to the visible spectrum. Therefore, the host material 610 itself attenuates none of the visible light and allows full or nearly full transmission of the visible spectrum. Therefore, the only effects on light attempting to pass through the host material 610 are due to the nanoparticles 620. In some embodiments, the nanoparticles 620 may be distributed substantially evenly throughout the host material 610. In other embodiments, the nanoparticles 620 may agglomerate, resulting in uneven distributions. For example, Ag nanoparticles may agglomerate when in solution, forming cluster of a nanoparticles that, in effect, act as larger particles affecting the LSPR behavior. The nanoparticles 620 may include a deagglomeration coating thereon to limit the agglomeration of the nanoparticles. The solution in which the nanoparticles 620 are dispersed may also include a deagglomeration agent.

Figure 7:
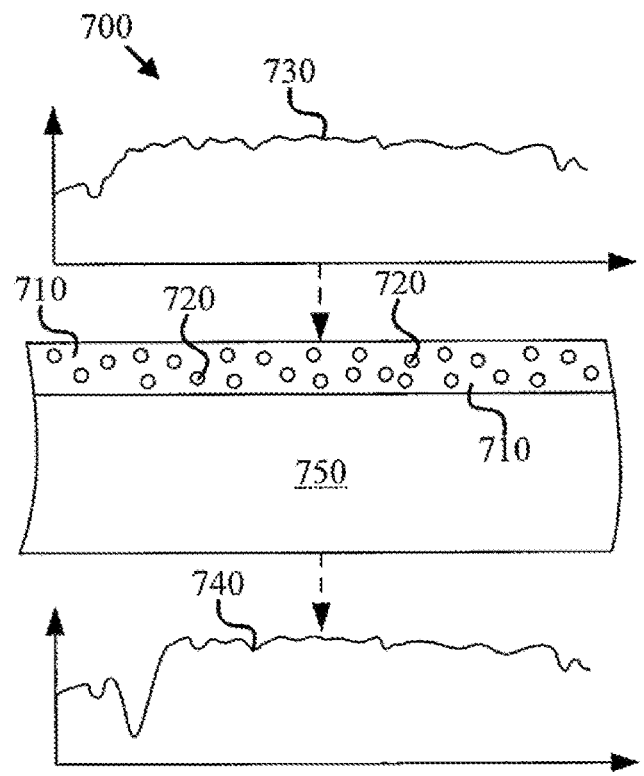
FIG. 7 is a schematic cross-sectional view illustration depicting another embodiment of a light filtering apparatus according to the present invention.

Likewise, the host material may be a coating 710 that may be, along with substrate 750, substantially transparent to the visible spectrum, as depicted in FIG. 7. In either situation, the host material 610, coating 710, substrate 750, or similar structures may be transparent or have independent light filtering or blocking characteristics. The nanoparticles 720 may agglomerate or otherwise cluster together during the application of the nanoparticles 720 and coating 710 to the substrate 750. To limit or, in some cases, prevent the clustering of the nanoparticles 720, the coating 710 may be applied in a thin film. In some embodiments, the thin film coating 710 may be applied to the substrate 750 by spin coating. Spin coating may allow the deposition of a uniform thickness of the coating 710 and nanoparticles 720 across the surface of the substrate 750. In other embodiments, the coating 710 may be applied to the substrate 750 by dip coating.

Spin coating creates a thin substantially uniform coating 710 by spinning the substrate 750 during application of the coating 710. The spinning of the substrate may cause the fluid coating 710 (and suspended nanoparticles 720) to move in a circular motion. The circular motion may provide the coating 710 and suspended nanoparticles 720 with inertia that urges the coating 710 and suspended nanoparticles 720 radially outward from a rotational axis. The force applied outward (commonly known as "centrifugal force") may be given by:

$$F_c = m \times r \times \omega^2$$

where $F_c$ is the centrifugal force, m is the mass of the coating, r is the distance from the rotational axis, and $\omega$ is the angular velocity in radians per second. The thickness of the coating 710 may decrease with increasing force and, therefore, with mass and the square of the angular velocity.

Dip coating may create a thicker coating 710 than spin coating by immersing the substrate 750 in a solution including suspended nanoparticles 720 for a period of time and then withdrawing the substrate from 750 from the solution. The thickness of the coating may be at least partially dependent upon the duration of the immersion, the rate of withdrawal of the substrate 750, and the viscosity of the solution. For example, a longer immersion in the solution may allow for a thinner the coating 710 that is deposited onto the substrate 750. The concentration of the nanoparticles 720 within the coating 710 may increase with longer immersion times. In another example, a faster withdrawal rate may decrease the thickness of coating 710 on the substrate 750.

Figure 7A:
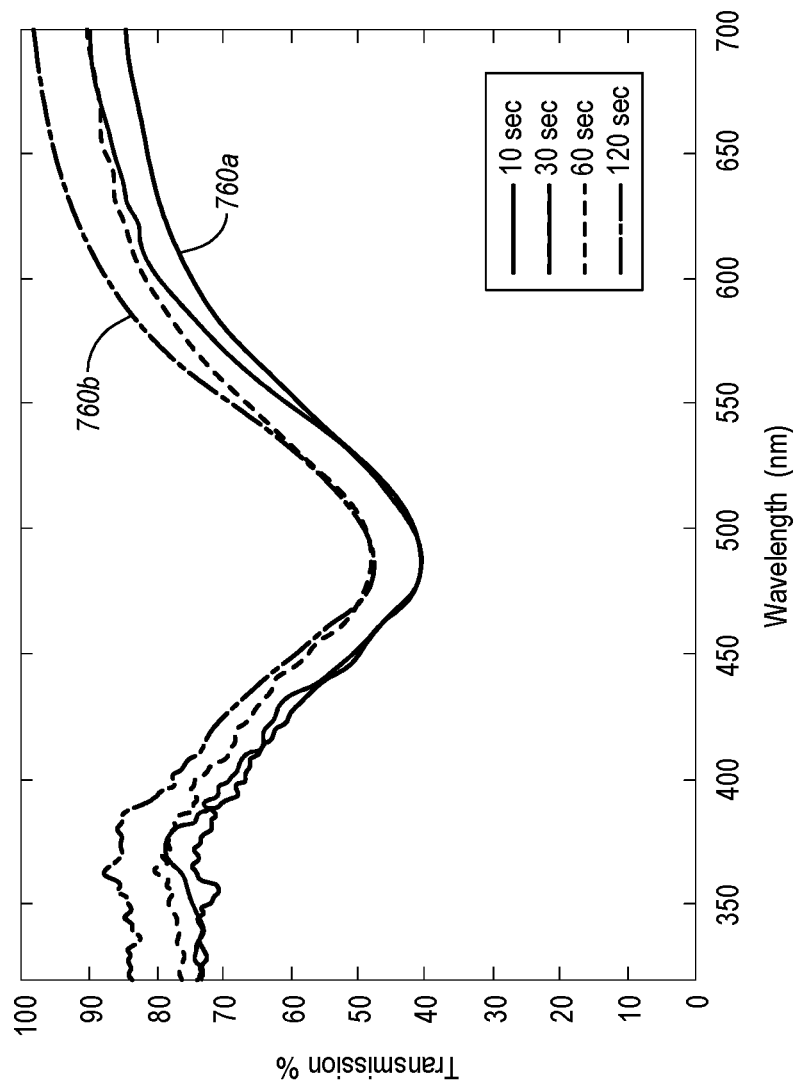
FIG. 7A is a graph depicting the measured transmission spectrum for a variety of immersion durations.

As shown in FIG. 7A, when employing, by way of example but without limitation, Ag nanoparticles having a major dimension of about 70 nm, the overall transmission of a filter increases as the duration of immersion increases. The thinner coating 710 allows a greater percentage of the incident light to be transmitted. FIG. 7A depicts the transmission spectrum of a 10 second, 30 second, 60 second, and 120 second immersion of a glass slide in PVA dissolved Ag nanoparticle solution. The Ag nanoparticles suspended in solution may be about 70 nm in diameter. In other embodiments, the nanoparticles may have other diameters and exhibit similar behavior. The 10 second immersion curve 760*a* may result in a lower overall transmission of light through the filter. The overall transmission may increase and the 120 second immersion curve 760*b* may transmit more overall light.

In an embodiment, it may be beneficial for a coating of nanoparticles intended to regulate neuroactive wavelengths be disposed within or upon a surface of a material, coating or substrate containing dye to reduce the transmission of light, such as in traditional sunglasses lenses. In such a situation, the dye may be chosen independently of its neuroactive wavelength regulating properties while the layered structure would still provide the aforementioned neurological benefits. In another embodiment, the material, coating, or substrate material may include other desirable additions, such as photochromic components. For example, this may result in a lens for eyeglasses that may alter its transmission characteristics across some or substantially all of the visible spectrum while maintaining optimal attenuation of the neuroactive wavelengths. Therefore, such a lens would be appropriate for use indoors or out.

Also depicted in FIGS. 6 and 7 are graphs 600, 700 with spectra representative of daylight at sea level of the incident light 630, 730 and the simulated transmitted light 640, 740 for the host material 610 with suspended nanoparticles 620 and the coating 710 with nanoparticles 720, respectively. In this example, the nanoparticles scatter and/or absorb wavelengths in the 480 nm range. In an embodiment, the optical notch filter may attenuate the target wavelength, such as 480 nm, and about 25 nm greater and less than the target wavelength, measured as a full-width half-maximum ("FWHM") of about 50 nm. In another embodiment, the notch filter may have a FWHM of about 50 nm to about 80 nm. In yet another embodiment, the notch filter may have a FWHM of less than about 100 nm. 480 nm is the wavelength that generates the maximum response from the ipRCGs; however, dispersed nanoparticles can regulate the transmission of other wavelengths, such as 590 nm or 620 nm, as well. In an embodiment, the nanoparticles may have a major dimension less than about 80 nm. In another embodiment, the nanoparticles may have a major dimension less than about 72 nm. In yet another embodiment, the nanoparticles may have a major dimension less than about 50 nm.

Figure 8:
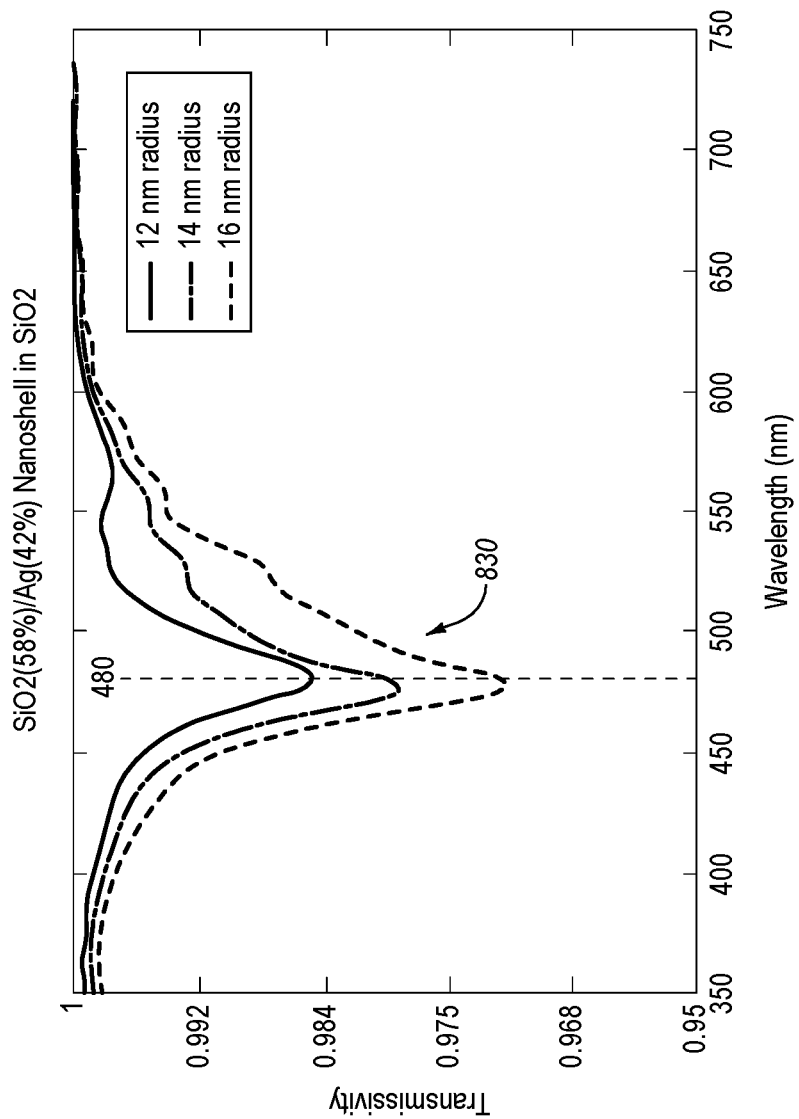
FIG. 8 is a cross-sectional view illustration depicting one embodiment of a core-shell nanoparticle and associated spectra in accordance with the present invention.
Figure 8:
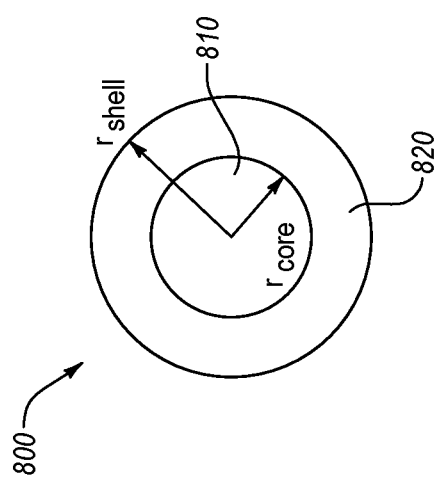

Referring now to FIG. 8, a core-shell nanoparticle 800 is shown having an inner core 810 with an outer shell 820. The depicted core-shell nanoparticle 800 is substantially spherical, but in other embodiments, a core-shell nanoparticle may have cross-sections including a circle, an ellipse, a rectangle, a hexagon, an octagon, or other polygon. The core and shell of the nanoparticle may differ in composition. In some embodiments, the inner core 810 may comprise one or more materials selected from a group consisting of a metal, a dielectric material, and a magnetic material. The inner core 810 may comprise a noble metal, a transition metal, a post transition metal, an alkali metal, or an alkaline earth metal. The noble metal may be silver, gold, or platinum. The transition metal may be copper, titanium, or zinc. The post-transition metal may be aluminum or gallium. The alkali metal may be sodium or potassium. The alkaline earth metal may be magnesium. The inner core 810 may also comprise an alloy of two or more of the aforementioned metals. In other embodiments, the inner core 810 may comprise a metal oxide, including $SiO_2$, $TiO_2$, $Al_2O_3$, or ZnO.

Likewise, any of the aforementioned metals, dielectric materials, or magnetic materials may be suitable as a material for the outer shell 820, as well. In some embodiments, the core may comprise $SiO_2$ and the outer shell 820 may comprise silver (Ag). In other embodiments, the core-shell nanoparticle 800 may comprise $SiO_2$ and Ag, where the $SiO_2$ is the material of the inner core 810 and accounts for about 58% of the radius. The remaining 42% of the radius is the Ag outer shell 820. The core-shell nanoparticle 800 may have other ratios between the inner core 810 and the outer shell 820, however, to tune the spectral response. In yet another embodiment, the inner core 810 may have a thickness of 16 nm. In a yet further embodiment, the outer shell 820 may have a thickness of 8 nm.

The extinction spectrum of a spherical nanoparticle may be calculated using the Mie scattering theory, which is partially dependent upon radius of the core-shell nanoparticle 800. As described in relation to FIG. 5G, the radius of a nanoparticle, therefore, can be used to fine-tune the spectral response 830 of the nanoparticle filter. In some embodiments, given a constant composition of the nanoparticles within the optical filter, the extinction spectrum of the filter may shift toward a longer wavelength with a larger average radius of the nanoparticles. In other embodiments, a larger average radius of the nanoparticles may attenuate a larger portion of the light.

In contrast to FIG. 5G, FIG. 8 depicts the effect of altering the radius of the core of a core-shell nanoparticle 800. There is little or no shift in the notch position, but rather only the amplitude and distribution of the curve about the peak position. Such a change in the distribution of material in the core-shell nanoparticle 800 may allow for the optimization of a notch filter by varying the amount of light attenuated without necessitating a change in medium or a change in size of the core-shell nanoparticles 800.

Furthermore, the density of the nanoparticles suspended in the material may be selected to achieve the desired rate of attenuation of the neuroactive wavelengths. One of skill in the art will understand that a higher density of nanoparticles will provide a higher rate of attenuation, but one may only increase attenuation rates this way until further concentration would lead to coupling of resonances between particles. To prevent agglomeration of the nanoparticles, the nanoparticles may include an anti-agglomeration shell or coating as described in relation to FIG. 6, such as polyvinylpyrrolidone.

The nanoparticles may be in solution with the host medium. The host medium may be a polymer suspension, such as polyvinylacetate, polymethylmethacrylate (PMMA), sol-gel, or similar medium. In an embodiment, the concentration of nanoparticles in the solution with the host medium is about 15% weight to volume. In another embodiment, the concentration of nanoparticles in the solution with the host medium is about 20% weight to volume. In yet another embodiment, the concentration of nanoparticles in the solution with the host medium is about $7.05 \times 10^{10}$ particles per cubic centimeter. In a yet further embodiment, nanoparticles in the solution with the host medium may have a molecular weight of between 30,000 and 100,000.

Figure 9:
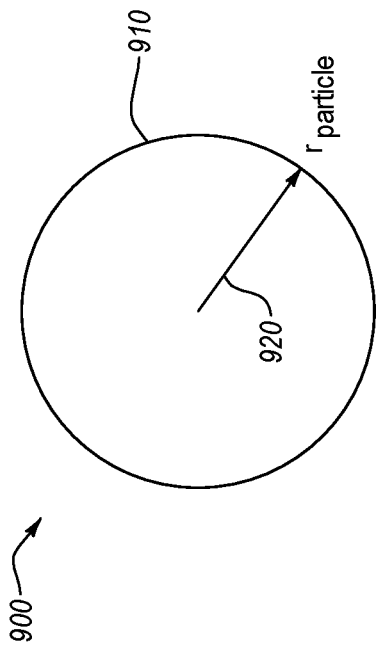
FIG. 9 is a cross-sectional view illustration depicting one embodiment of a metallic nanoparticle and associated spectra in accordance with the present invention.
Figure 9:
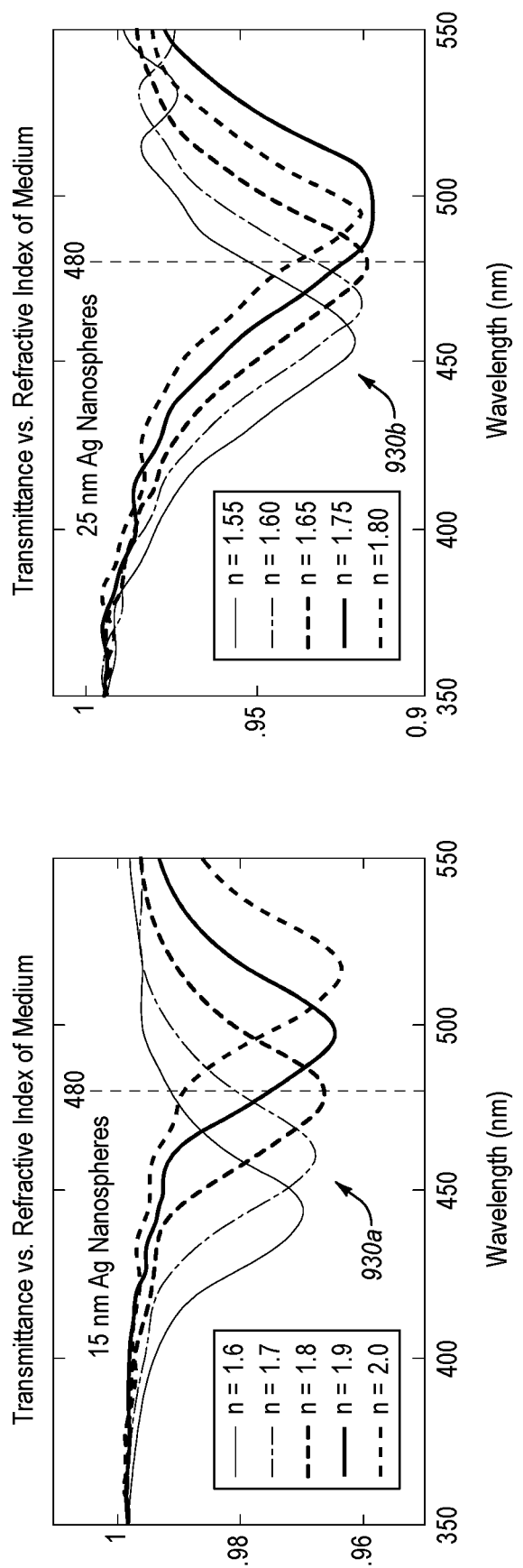
Figure 9A:
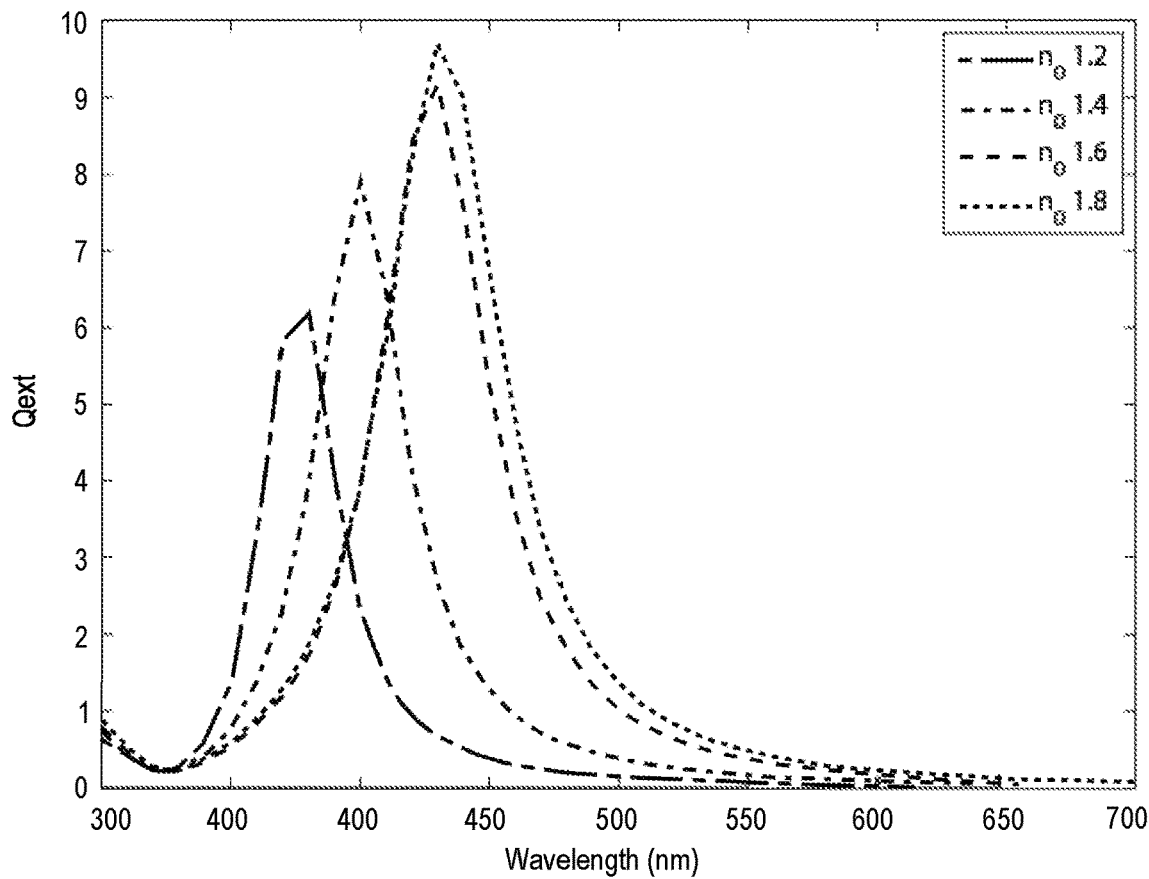
FIG. 9A is a plot of simulated extinction efficiencies for spherical particles in solution with different media.

Additionally, the medium selected for the bulk material or coating material in which the nanoparticles are suspended will shift the response spectrum. Referring now to FIG. 9, a nanosphere 900 is shown comprising a single material 910 with a radius 920. In an embodiment, the nanosphere 900 may comprise one or more of the materials described for use in the inner core 810 of a core-shell nanoparticle 800 mentioned above. The spectral responses of 15 nm Ag nanospheres 930a and 25 nm Ag nanospheres 930b are dependent on both the index of refraction of the bulk material or coating medium in which the nanosphere is suspended. FIG. 9a depicts the effect of medium refractive index on the simulated spectral response of a spherical 30 nm Ag nanoparticle. As the refractive index of the medium increases, the wavelength attenuated by the notch filter increases. In various embodiments, the index of refraction of the medium may be less than about 1.5, about 1.5, or greater than about 1.5. As discussed earlier, an increase in the radius of the nanosphere results in increased attenuation, but also shifts the spectral response. However, a change in the index of refraction of the medium enables the spectral response to be shifted back toward the desired wavelength, in this case, 480 nm.

Figure 9B:
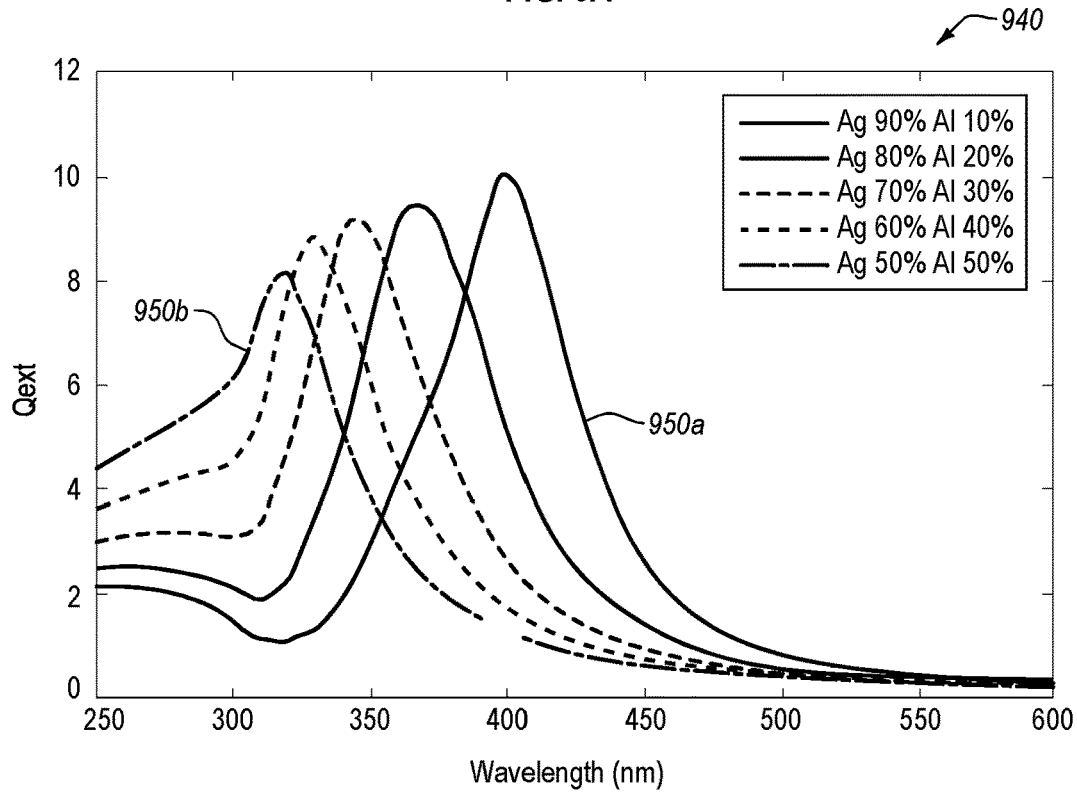
FIG. 9B is a plot of simulated extinction efficiencies for particles of varying alloying percentages.

A nanoparticle 900 with a single radius 910 (i.e., a substantially homogenous nanoparticle) may exhibit a variety of extinction coefficients. Varying the alloying percentage of materials in the nanoparticle 900 while maintaining a constant radius 910 may shift the wavelength attenuated by a notch filter. For example, FIG. 9B is a graph illustrating the effects of variations in alloying percentage of a nanoparticle including a silver-aluminum alloy metal (AgXXAlXX, where XX is a percentage composition). The coefficient of extinction for each composition may blue-shift as the percentage of aluminum in the alloy increases. For example, the Ag90Al10 curve 950a has a local maximum at about 400 nm, and the Ag50Al50 curve 950b has a local maximum at about 320 nm.

It should be understood that the examples thus far have described an optical notch filter comprising a unimodal distribution of nanoparticles in order to attain a high Q factor and attenuate a single wavelength or narrow range of wavelengths. However, the use of an optical notch filter is not exclusive to one wavelength, and the use of nanoparticles of different shapes, compositions, or sizes is possible for the selective attenuation of more than one wavelength.

This may be accomplished either by homogenous dispersion of nanoparticles with more than one composition, shape, and/or size, or by layering of coating materials with one or more particular species of nanoparticle. For example, a filter may be produced with the 25 nm Ag nanospheres of FIG. 8 to attenuate light in the 480 nm range of the spectrum with other nanoparticles appropriate to attenuate light in another range of the spectrum, each of the species distributed homogenously. Alternatively, a first coating appropriate for attenuating light in a first range, such as the 480 nm range, could be applied to surface of an eyeglasses lens, while a second coating appropriate for attenuating light in a second range could then be applied to another surface of the lens or layered on top of the first coating. Whether applied singularly or in combinations, each coating may have a thickness greater than about 5 μm. In another embodiment, the coating may have a thickness of about 6 μm. In another embodiment, the coating may have a thickness of about 11 μm.

The thickness of the coating and the distribution of nanoparticles within the coating may be controlled by the deposition method of the coating. In an embodiment, the application of the coating may comprise a spin coating step. In another embodiment, the application of the coating may comprise a dip coating step. In yet another embodiment, the application of the coating may comprise a deagglomeration step, which, itself, may comprise ultrasonic dispersion.

Figure 10:
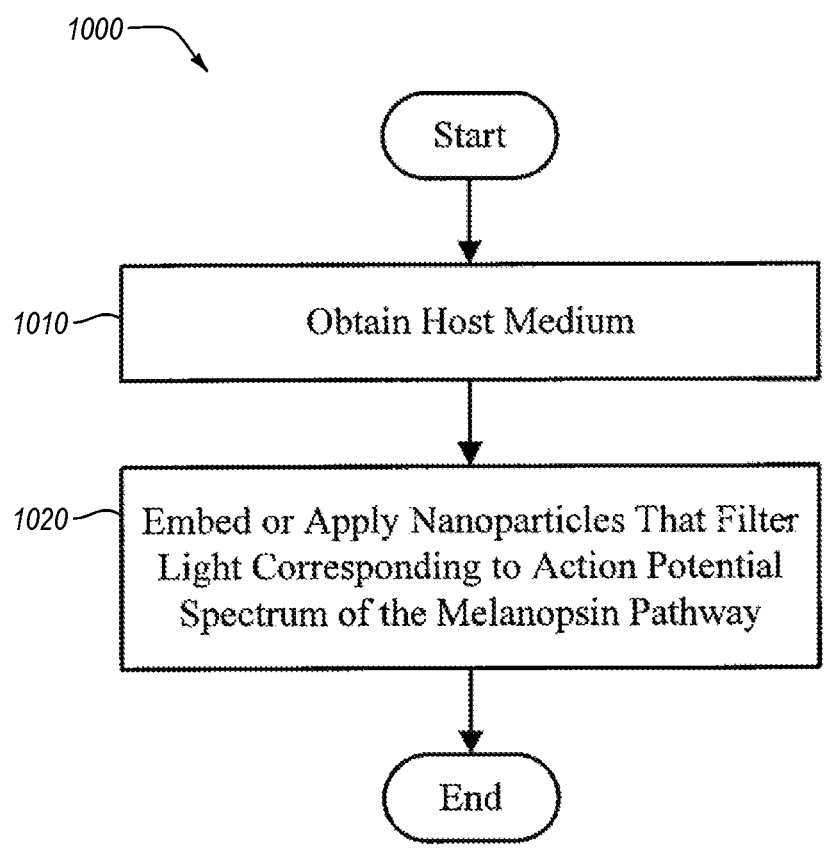
FIG. 10 is a flowchart diagram of one method of mitigating a photoresponsive medical condition in accordance with the present invention.

FIG. 10 depicts a method 1000 of producing an optical notch filter to reduce or alleviate symptoms affiliated with exposure to neuroactive wavelengths. As shown, the method includes at least obtaining 1010 a host medium and embedding or applying 1020 nanoparticles therein or thereon that filter light corresponding to the action potential spectrum of the melanopsin pathway. Additional steps of the method may include determining a desired central frequency of the filter, determining a desired full width half maximum of the filter, or varying the size of the plurality or composition of the nanoparticles. In addition, the manufacturing process may include varying the composition of the host medium. Depending on the host medium used, the method of manufacture may optionally include removing bubbles from a solution of the host medium and nanoparticles.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A method for reducing the frequency and/or severity of photophobic responses or for modulating circadian cycles, the method comprising:
   receiving an amount of light across a visible spectrum;
   introducing an optical filter to the path of the light, the optical filter comprising a plurality of nanoparticles dispersed within a host material, wherein a concentration of the plurality of nanoparticles in the host material is about 15% weight to volume, about 20% weight to volume, or about $7.05 \times 10^{10}$ particles per cubic centimeter; and
   attenuating a portion of the spectrum associated with absorption by melanopsin ganglion cells such that a figure of merit greater than 1 is achieved, wherein the figure of merit is defined as a ratio of attenuation of light weighted across an action potential spectrum of a melanopsin pathway to attenuation of light weighted across a visual spectral response.

2. The method of claim 1, wherein the plurality of nanoparticles exhibit local surface plasmon resonance when exposed to the portion of the spectrum associated with absorption by melanopsin ganglion cells.

3. The method of claim 1, wherein attenuating a portion of the spectrum comprises attenuating light having a central wavelength of 480 nm, 590 nm, or 620 nm.

4. The method of claim 3, wherein the optical filter has a full width half maximum of less than 100 nm at the central wavelength.

5. The method of claim 3, wherein the optical filter has a full width half maximum of greater than 50 nm and less than 100 nm at the central wavelength.

6. The method of claim 3, wherein the optical filter has a full width half maximum of greater than 50 nm and less than 80 nm at the central wavelength.

7. The method of claim 1, wherein a figure of merit greater than 1.5 is achieved.

8. A method for reducing the frequency and/or severity of photophobic responses or for modulating circadian cycles, the method comprising:
   receiving an amount of light across a visible spectrum;
   introducing an optical filter to the path of the light, the optical filter comprising a plurality of nanoparticles dispersed within a host material such that the optical filter is configured to attenuate light having a central wavelength of 480 nm, 590 nm, or 620 nm, wherein the plurality of nanoparticles have a concentration in the host medium of about 15% to 20% weight to volume; and
   attenuating light at the central wavelength such that a figure of merit greater than 1.5 is achieved, wherein the figure of merit is defined as a ratio of attenuation of light weighted across an action potential spectrum of a melanopsin pathway to attenuation of light weighted across a visual spectral response.

9. The method of claim 8, wherein the optical filter has a full width half maximum of greater than 50 nm and less than 100 nm at the central wavelength.

10. The method of claim 8, wherein the optical filter has a full width half maximum of 80 nm at the central wavelength.

11. A method for reducing the frequency and/or severity of photophobic responses or for modulating circadian cycles, the method comprising:
    receiving an amount of light across a visible spectrum;
    introducing an optical filter to the path of the light, the optical filter comprising a plurality of nanoparticles dispersed within a host material, wherein the concentration of the plurality of nanoparticles in the host material is about $7.05 \times 10^{10}$ particles per cubic centimeter; and attenuating a portion of the spectrum associated with absorption by melanopsin ganglion cells such that a figure of merit greater than 1 is achieved, wherein the figure of merit is defined as a ratio of attenuation of light weighted across an action potential spectrum of a melanopsin pathway to attenuation of light weighted across a visual spectral response.

12. The method of claim 11, wherein the plurality of nanoparticles exhibit local surface plasmon resonance when exposed to the portion of the spectrum associated with absorption by melanopsin ganglion cells.

13. The method of claim 11, wherein attenuating a portion of the spectrum comprises attenuating light having a central wavelength of 480 nm, 590 nm, or 620 nm.

14. The method of claim 13, wherein the optical filter has a full width half maximum of less than 100 nm at the central wavelength.

15. The method of claim 13, wherein the optical filter has a full width half maximum of greater than 50 nm and less than 100 nm at the central wavelength.

16. The method of claim 13, wherein the optical filter has a full width half maximum of greater than 50 nm and less than 80 nm at the central wavelength.

17. The method of claim 11, wherein a figure of merit greater than 1.5 is achieved.

* * * * *